(12) United States Patent
Plumptre et al.

(10) Patent No.: US 8,728,043 B2
(45) Date of Patent: *May 20, 2014

(54) DRIVE MECHANISM FOR A DRUG DELIVERY DEVICE

(75) Inventors: David Aubrey Plumptre, Worcestershire (GB); Christopher John Jones, Gloucestershire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 584 days.

This patent is subject to a terminal disclaimer.

(21) Appl. No.: 12/788,699

(22) Filed: May 27, 2010

(65) Prior Publication Data

US 2010/0331806 A1    Dec. 30, 2010

Related U.S. Application Data

(60) Provisional application No. 61/182,842, filed on Jun. 1, 2009.

(30) Foreign Application Priority Data

Jul. 10, 2009  (EP) .................................. 09009050

(51) Int. Cl.
*A61M 5/00*    (2006.01)
(52) U.S. Cl.
USPC ........................................................... 604/207
(58) Field of Classification Search
USPC ........................................................... 604/207
See application file for complete search history.

(56) References Cited

U.S. PATENT DOCUMENTS

| | | |
|---|---|---|
| 3,302,462 A | 2/1967 | Pursell |
| 5,423,752 A | 6/1995 | Haber et al. |
| 5,514,097 A | 5/1996 | Knauer |
| 5,584,815 A | 12/1996 | Pawelka et al. |
| 5,591,136 A | 1/1997 | Gabriel |
| 5,792,117 A | 8/1998 | Brown |
| 5,820,602 A | 10/1998 | Kovelman et al. |
| 6,090,080 A | 7/2000 | Jost et al. |
| 6,936,032 B1 | 8/2005 | Bush, Jr. et al. |
| 2004/0127858 A1 | 7/2004 | Bendek et al. |

(Continued)

FOREIGN PATENT DOCUMENTS

| | | |
|---|---|---|
| DE | 93 01 334 U1 | 4/1993 |
| DE | 197 30 999 C1 | 12/1998 |

(Continued)

OTHER PUBLICATIONS

Machine Deisgn, Penton Media, vol. 65, No. 11 (1993) p. 36 "Standard Compression Springs Save Space".

*Primary Examiner* — Jason Flick
(74) *Attorney, Agent, or Firm* — McDonnell Boehnen Hulbert & Berghoff LLP

(57) ABSTRACT

A dose setting mechanism for a drug delivery device is disclosed. The mechanism comprises an outer housing and an inner housing having an external groove. The inner housing guides a driver having either a blocking or locking member disposed inside the driver that can lock a flexible tab to an internal groove during dose delivery in the inner housing such that the driver follows the path of the groove and to advance a spindle to move a cartridge bung. A dial sleeve is disposed between the outer and inner housing and is rotatably engaged with the inner housing.

14 Claims, 3 Drawing Sheets

(56) References Cited

U.S. PATENT DOCUMENTS

| | | |
|---|---|---|
| 2004/0162528 A1 | 8/2004 | Horvath et al. |
| 2004/0186437 A1 | 9/2004 | Frenette et al. |
| 2004/0210199 A1 | 10/2004 | Atterbury et al. |
| 2004/0236285 A1 | 11/2004 | Fisher et al. |
| 2005/0137571 A1 | 6/2005 | Hommann |
| 2006/0153693 A1 | 7/2006 | Fiechter et al. |
| 2006/0258988 A1* | 11/2006 | Keitel et al. .................. 604/181 |
| 2007/0021718 A1 | 1/2007 | Burren et al. |
| 2008/0027397 A1 | 1/2008 | DeRuntz et al. |
| 2008/0077095 A1 | 3/2008 | Kirchhofer |
| 2008/0208123 A1 | 8/2008 | Hommann |
| 2009/0227959 A1 | 9/2009 | Hirschel et al. |

FOREIGN PATENT DOCUMENTS

| | | |
|---|---|---|
| DE | 298 18 721 U1 | 3/2000 |
| DE | 10 2005 063 311 A1 | 8/2006 |
| DE | 10 2005 060 928 A1 | 6/2007 |
| DE | 10 2006 038 123 A1 | 2/2008 |
| DE | 10 2007 026 083 A1 | 11/2008 |
| EP | 0 897 728 A1 | 2/1999 |
| EP | 0 937 471 A2 | 8/1999 |
| EP | 0 937 472 A2 | 8/1999 |
| EP | 1 541 185 A1 | 6/2005 |
| EP | 1 776 975 A2 | 4/2007 |
| EP | 1 923 084 A1 | 5/2008 |
| GB | 2 443 390 A | 5/2008 |
| WO | 92/18180 A1 | 10/1992 |
| WO | 93/07922 A1 | 4/1993 |
| WO | 96/23973 A1 | 8/1996 |
| WO | 96/39214 A1 | 12/1996 |
| WO | 97/10864 A1 | 3/1997 |
| WO | 99/03520 A1 | 1/1999 |
| WO | 01/19434 A1 | 3/2001 |
| WO | 03/080160 A1 | 10/2003 |
| WO | 2004/020028 A1 | 3/2004 |
| WO | 2004/064902 A1 | 8/2004 |
| WO | 2004/078241 A1 | 9/2004 |
| WO | 2004/078242 A2 | 9/2004 |
| WO | 2004/078293 A1 | 9/2004 |
| WO | 2005/018721 A1 | 3/2005 |
| WO | 2005/021072 A1 | 3/2005 |
| WO | 2005/044346 A2 | 5/2005 |
| WO | 2005/123159 A2 | 12/2005 |
| WO | 2006/024461 A1 | 3/2006 |
| WO | 2006/058883 A2 | 6/2006 |
| WO | 2006/079481 A1 | 8/2006 |
| WO | 2006/089767 A1 | 8/2006 |
| WO | 2006/114395 A1 | 11/2006 |
| WO | 2006/125328 A1 | 11/2006 |
| WO | 2007/017052 A1 | 2/2007 |
| WO | 2007/067889 A1 | 6/2007 |
| WO | 2008/031235 A1 | 3/2008 |
| WO | 2008/074897 A1 | 6/2008 |
| WO | 2008/116766 A1 | 10/2008 |
| WO | 2008/128373 A1 | 10/2008 |

* cited by examiner

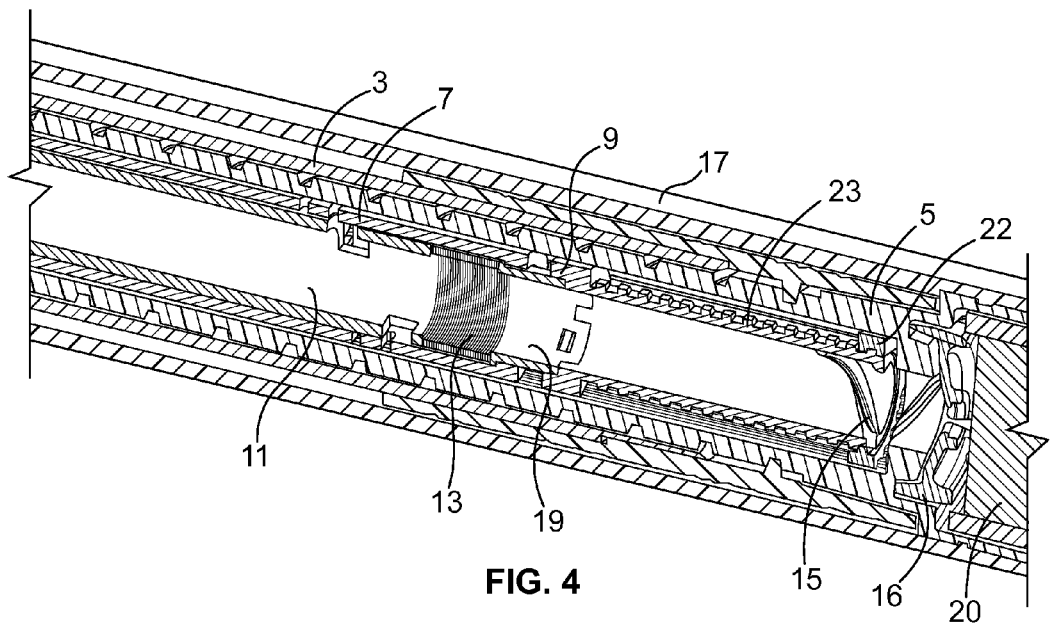
FIG. 4
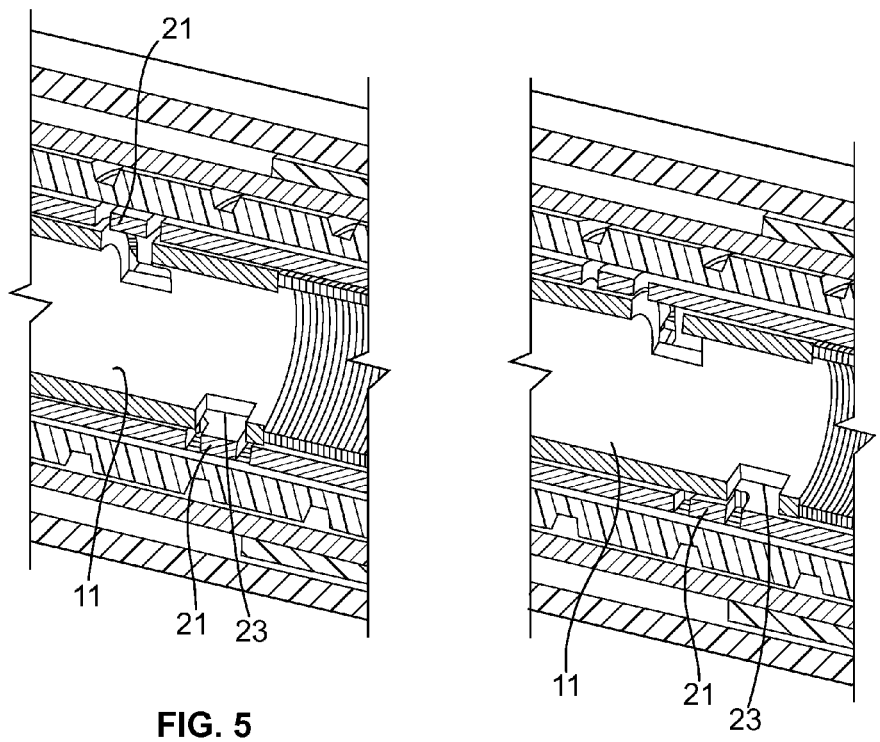
FIG. 5
FIG. 6

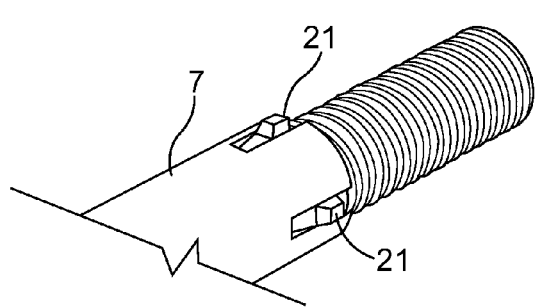
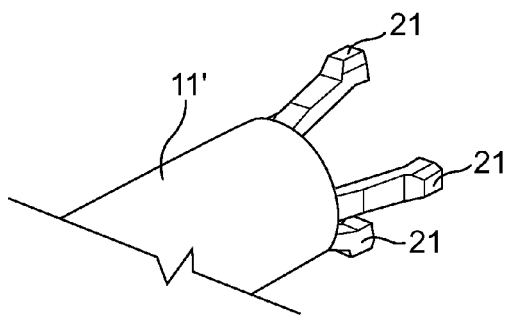
FIG. 7  FIG. 8
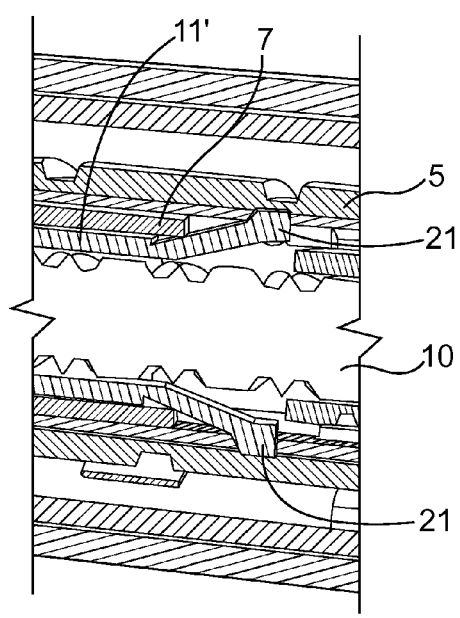
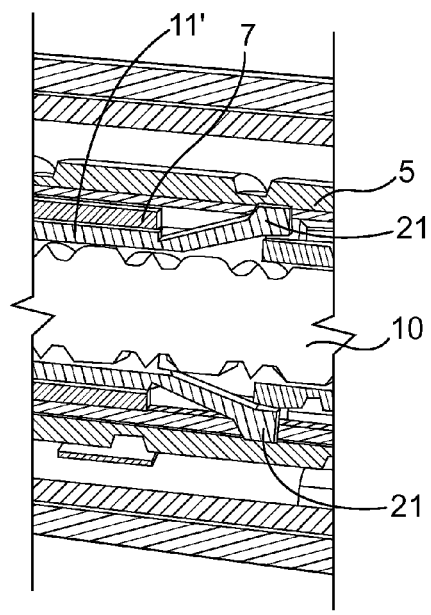
FIG. 9  FIG. 10

DRIVE MECHANISM FOR A DRUG DELIVERY DEVICE

BACKGROUND

1. Field of the Present Patent Application

The present application is generally directed to dose setting mechanisms for drug delivery devices. More particularly, the present application is generally directed to a dose setting mechanism comprising a stationary inner housing having a driver positioned inside the inner housing and having a slidable locking or blocking member that locks a flexible tab to an internal groove in the inner housing such that the driver follows the path of the groove during drug dispensing (injection).

2. Background

Pen type drug delivery devices have application where regular injection by persons without formal medical training occurs. This may be increasingly common among patients having diabetes where self-treatment enables such patients to conduct effective management of their disease.

There are basically two types of pen type delivery devices: resettable devices (i.e., reusable) and non-resettable (i.e., disposable). These types of pen delivery devices (so named because they often resemble an enlarged fountain pen) are generally comprised of three primary elements: (i) a cartridge section that includes a cartridge often contained within a housing or holder; (ii) a needle assembly connected to one end of the cartridge section; and (iii) a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then a dose is administered. Such removable needle assemblies may be threaded onto, or pushed (i.e., snapped) onto the pierceable seal end of the cartridge assembly.

The dosing section or dose setting mechanism is typically the portion of the pen device that is used to set a dose. During an injection, a spindle contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

Different types of pen delivery devices, including disposable (i.e., non-resettable) and reusable (i.e., resettable) varieties, have evolved over the years. For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism.

In contrast to typical disposable pen type devices, typical reusable pen delivery devices feature essentially two main reusable components: a cartridge holder and a dose setting mechanism. After a cartridge is inserted into the cartridge holder, this cartridge holder is attached to the dose setting mechanism. The user uses the dose setting mechanism to select a dose. Before the user injects the set dose, a replaceable double-ended needle assembly is attached to the cartridge housing.

This needle assembly may be threaded onto or pushed onto (i.e., snapped onto) a distal end of the cartridge housing. In this manner, a double ended needle mounted on the needle assembly penetrates through a pierceable seal at a distal end of the cartridge. After an injection, the needle assembly is removed and discarded. After the insulin in the cartridge has been exhausted, the user detaches the cartridge housing from the dose setting mechanism. The user can then remove the empty cartridge from the cartridge retainer and replace the empty cartridge with a new (filled) cartridge.

Aside from replacing the empty cartridge with a new cartridge, the user must somehow prepare the dose setting mechanism for a new cartridge: the dose setting mechanism must be reset to a starting or initial position. For example, in certain typical resettable devices, in order to reset the dose setting mechanism, the spindle that advances in a distal direction during dose injection must somehow be retracted back into the dose setting mechanism. Certain known methods of retracting this spindle back into the dose setting mechanism to a restart or an initial position are known in the art. As just one example, known reset mechanisms require a user to turn back or push back (retract) the spindle or some other portion of the dose setting mechanism.

Resetting of known dose setting mechanisms have certain perceived disadvantages. One perceived disadvantage is that the pen device user has to disassemble the device to either remove an empty cartridge or somehow reset the device. As such, another perceived disadvantage is that such devices have a high number of parts and therefore such devices are typically complicated from a manufacturing and from an assembly standpoint. For example, certain typical resettable pen type devices are not intuitive as to how a user must replace an empty cartridge and reset the device. In addition, because such resettable devices use a large number of components parts, such resettable devices tend to be large and bulky, and therefore not easy to carry around or easy to conceal.

There is, therefore, a general need to take these disadvantages associated with resetting issues into consideration in the design and development of resettable drug delivery devices. Such desired drug delivery devices would tend to reduce the number of component parts and also tend to reduce manufacturing costs while also making the device less complex to assemble and manufacture. Such desired devices would also tend to simplify the steps required for a user to reset a dose setting mechanism while also making the device less complex and more compact in size.

SUMMARY

According to an exemplary arrangement, my invention is directed to a drug delivery device having a driver locking feature comprising a cartridge holder containing a cartridge of medicament connected to a dose dialing assembly. The cartridge contains a bung or piston that is acted upon by a spindle during dose delivery. The dose dialing assembly comprises an outer housing and an inner stationary housing, where the inner housing has at least one internal groove running along the axis of the inner surface. The assembly contains a driver positioned within the inner housing and a flexible tab that engages the internal groove to form a detent during dose dialing. Inside the driver is a blocking member that can slide and lock the flexible tab in the groove during dose dispensing such that the driver is forced to follow the path of the groove. The flexible tab can be part of the driver, preferably located near the distal end of the driver, or it can be a stand-alone component. Preferably my invention comprises two or more flexible tabs. The tabs can be manufactured from any flexible material, preferably using a material that can form a detent with the groove in the inner housing during dose setting and most preferably to provide both a tactile and audile feedback to the user.

In another embodiment, the blocking member has an aperture that is aligned with the flexible tab when the blocking member is in a non-locked position and is misaligned with the flexible tab when in the locked position. When misaligned, the flexible tab is locked in the groove. The groove can be parallel to the axis of the inner housing or it can be helical. When the groove is parallel, the driver will not rotate during dose injection and when the groove is helical, the driver will rotate following the path of the groove during dose injection.

My invention also relates to a method of setting and injecting a dose of medicament with a drug delivery device that comprises a first step where a user holds a dosing assembly of an injection device as described above and rotates the driver in a first direction to set a dose. During dose setting the driver rotates relative to the external and inner housings and the flexible tab overrides the internal groove. Once the dose is set, the user pushes an injection button that is clutched to the driver to cause the driver to move distally in a second direction. This action also moves the blocking member in an axial distal direction to a locked position to engage the flexible tab causing it to non-releasably engage the internal groove. This causes the driver to follow the path of the groove while moving distally in the second direction and ultimately expels medicament from the drug delivery device.

Yet another embodiment of my drug delivery device that has a drive sleeve lockout feature is one where there is a locking member slidably positioned inside the driver that has an associated flexible tab that engages the internal groove to form a detent during dose dialing. When in a locked position during dose dispensing the flexible tab is locked in engagement with the groove such that the driver follows the path of the groove. The flexible member can engage the groove through an aperture in the driver and when in the locked position, the tab is biased into the groove by the misaligned driver aperture.

Another embodiment is a method of setting and injecting a dose of medicament with an injection device having a driver lockout feature where rotation of the driver in the first direction during dose setting relative to the housing causes the flexible tab associated with the locking element to releasably engage and override the groove causing an audible click. Once the dose is set the user pushes an injection button to inject a set dose that advances the driver in a second direction and moves the locking member in an axial distal direction so that the flexible tab is locked in engagement with the groove. This causes the driver to follow the path of the groove ultimately expelling medicament from the drug delivery device.

In each of the embodiments described a dial sleeve is disposed between the outer and inner housing and is rotatably engaged with an external groove of the inner housing. This engagement may include a nut that is rotatably fixed to the dose dial sleeve and threadedly engaged to the external groove on the inner housing. When setting a dose, the dial sleeve is rotated with respect to both the outer housing and the inner housing. The dial sleeve is translated away in the proximal direction from both the outer housing and the inner housing. The locking or blocking members can be biased in the proximal direction during dose setting so that the tabs form a detent. During the dose injection step the biasing member, preferably a spring, is overcome by the force exerted when the user pushes the injection button.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 4 illustrates a cross sectional view of one embodiment of the drive mechanism illustrating the blocking member engaging two flexible tabs to lock them into the groove in the inner housing;

FIG. 5 is a close-up of the cross sectional view of one embodiment of the drive mechanism illustrated in FIG. 4 showing the blocking member in a non-locked position and two flexible tabs forming a detent with the groove in the inner housing;

FIG. 6 is a close-up of the cross sectional view of one embodiment of the drive mechanism illustrated in FIG. 4 showing the blocking member in a locked position and two flexible tabs locked with the groove in the inner housing;

FIG. 7 is a perspective view of the driver of an alternative embodiment of the drive mechanism on our invention showing two flexible tabs protruding through apertures in the driver during dose setting;

FIG. 8 is a perspective view of the locking member having three flexible tabs associated therewith at its distal end;

FIG. 9 is a close-up of the cross sectional view of an alternative embodiment of the drive mechanism of our invention showing the locking member in an un-locked position and two flexible tabs forming a detent with the groove; and FIG. 10 is a close-up of the cross sectional view of an alternative embodiment of the drive mechanism of our invention showing the locking member in a locked position and two flexible tabs locked with the groove in the inner housing.

DETAILED DESCRIPTION

Figure 1:
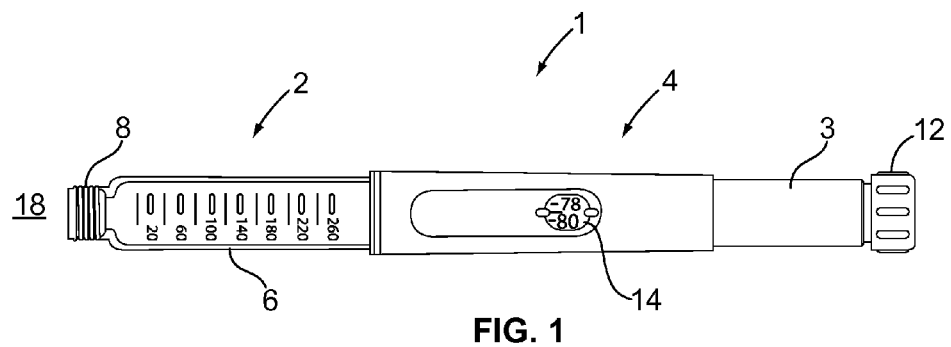
FIG. 1 illustrates an embodiment of a resettable drug delivery device.

Referring to FIG. 1, there is shown a drug delivery device 1 in accordance with an exemplary arrangement. The drug delivery device 1 comprises a housing having a first cartridge retaining part 2, and a dose setting mechanism 4. The drug delivery device may be a resettable drug delivery device (i.e., a reusable device) or alternatively a non-resettable drug delivery device (i.e., a non-reusable device). A first end of the cartridge retaining part 2 and a second end of the dose setting mechanism 4 are secured together by connecting features. For non-resettable devices, these connecting features would be permanent and non-reversible. For resettable devices, these connecting features would be releasable.

In this illustrated arrangement, the cartridge housing 2 is secured within the second end of the dose setting mechanism 4. A removable cap (not shown) is releasably retained over a second end or distal end of a cartridge retaining part or cartridge housing. The dose setting mechanism 4 comprises a dose dial grip 12 and a window or lens 14. A dose scale arrangement is viewable through the window or lens 14. To set a dose of medication contained within the drug delivery device 1, a user rotates the dose dial grip 12 such that a dialed dose will become viewable in the window or lens 14 by way of the dose scale arrangement.

FIG. 1 illustrates the medical delivery device 1 with the cover cap removed from a distal end 18 of the medical delivery device 1. This removal exposes the cartridge housing 6. Preferably, a cartridge (not shown) from which a number of doses of a medicinal product may be dispensed, is provided in the cartridge housing 6. Preferably, the cartridge contains a type of medicament that can be administered relatively often, such as once or more times a day. One such medicament is either long acting or short acting insulin or an insulin analog. The cartridge comprises a bung or stopper that is retained near a second end or a proximal end of the cartridge. The medical delivery device also comprises a driver 7, preferably having at least two portions, 7 and 9 (see FIG. 4), and a spindle 10 (see FIG. 9), that is in threaded engagement 15 with the distal portion of the driver 9.

The cartridge housing 6 has a distal end and a proximal end. Preferably, the distal end of the cartridge housing 6 comprises a hub 8 for attaching a removable needle assembly. However, other needle assembly connection mechanisms could also be used. If the drug delivery device 1 comprises a resettable device, the cartridge proximal end is removably connected to the dose setting mechanism 4. In one preferred embodiment, the cartridge housing proximal end is removably connected to the dose setting mechanism 4 via a bayonet connection. However, as those of ordinary skill in the art will recognize, other types of removable connection methods such as threads, partial threads, ramps and detents, snap locks, snap fits, and luer locks may also be used.

As previously mentioned, the dose setting mechanism 4 of the drug delivery device illustrated in FIG. 1 may be utilized as a reusable drug delivery device. (i.e., a drug delivery device that can be reset) Where the drug delivery device 1 comprises a reusable drug delivery device, the cartridge is removable from the cartridge housing 6. The cartridge may be removed from the device 1 without destroying the device 1 by merely having the user disconnect the dose setting mechanism 4 from the cartridge housing 6.

In use, once the cap is removed, a user can attach a suitable needle assembly to the hub 8 provided at the distal end of the cartridge housing 6. Such needle assembly may be, for example, screwed onto a distal end of the housing 6 or alternatively may be snapped onto this distal end. After use, the replaceable cap may be used to re-cover the cartridge housing 6. Preferably, the outer dimensions of the replaceable cap are similar or identical to the outer dimensions of the dose setting mechanism 4 so as to provide an impression of a unitary whole when the replaceable cap is in position covering the cartridge housing 6 when the device is not in use.

FIG. 4 illustrates a perspective, cross sectional view of one arrangement of a dose setting mechanism 4. Those of skill in the art will recognize that dose setting mechanism 4 may include a connection mechanism for releasably connecting to a cartridge holder, like the cartridge holder 6 illustrated in FIG. 1. However, as those of ordinary skill in the art will recognize, the dose setting mechanism may also include a permanent connection mechanism for permanently connecting to a cartridge holder. The dose setting mechanism 4 comprises an outer housing 17 containing a number (or dose dialing) sleeve 3, a stationary inner housing 5, a connector 19, a proximal driver portion 7, a distal driver portion 9, and a biasing member, preferably a compression spring 13. A spindle 10 (see FIG. 10) may engage thread 15 inside the distal driver 9 and that is connected to pressure plate 16 that abuts cartridge bung 20. In one arrangement, the spindle can be generally circular in cross section however other arrangements and shapes may also be used.

Figure 2:
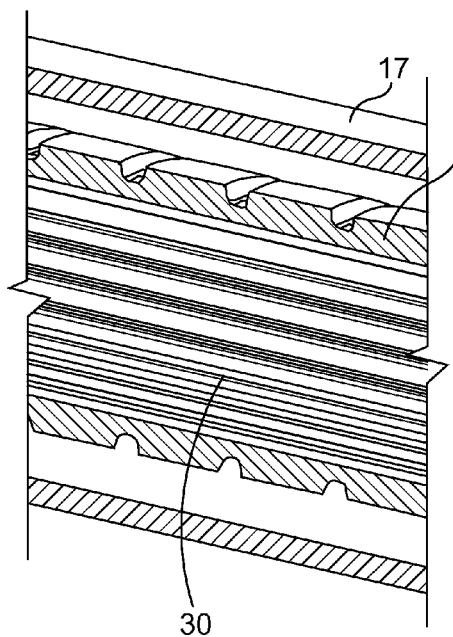
FIG. 2 illustrates a cross sectional view of one embodiment of the drive mechanism to specifically illustrate the linear shape of the at least one groove on the internal surface of the inner housing.
Figure 3:
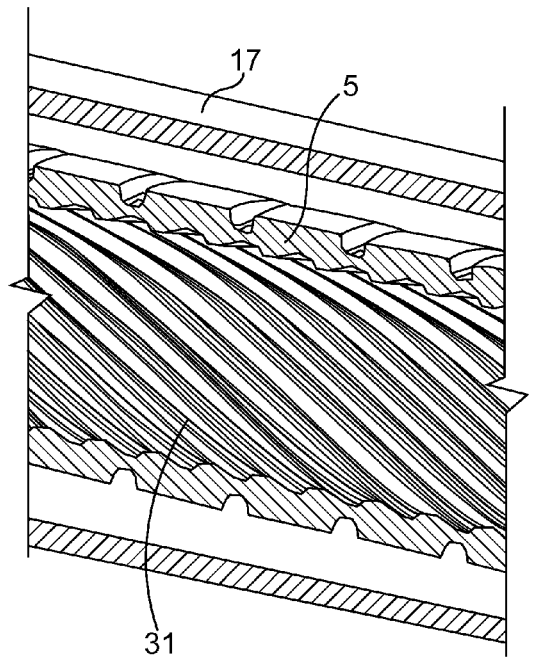
FIG. 3 illustrates a cross sectional view of one embodiment of the drive mechanism to specifically illustrate the helical shape of the at least one groove on the internal surface of the inner housing.

Both the proximal and distal driver portions are positioned inside the stationary inner housing 5. The inner housing has at least one groove on its inner surface, most preferably a series or set of grooves running along the axis of the inner housing. FIGS. 2 and 3 show two preferred designs for the grooves, linear grooves 30 (FIG. 2) and helical grooves 31 (FIG. 3). Returning to FIG. 4 the proximal driver has an associated flexible tab 21. In the embodiment shown, there are two flexible tabs and two corresponding apertures 23 in blocking member 11 that allow the flexible tabs to flex into forming a detent with the grooves on the inner housing 5. This detent or clicker provides the user with an audible and tactile feedback as a dose is set because the flexible tab overrides the grooves as the driver 7 is rotated outwardly (proximally) with the dial sleeve 3. This shown in FIG. 5. FIGS. 4 and 6 shows the blocking member 11 in its locked position, urged distally forward during dose delivery, thus locking flexible tabs 21 into the grooves of the inner housing and ensuring that the driver follows the path of the grooves.

During dose delivery, blocking member 11 is urged or slid distally compressing biasing component 13, which during dose setting biases the blocking member proximally preventing the flexible tabs from locking with the grooves. This sliding distal movement of the locking member during dose delivery constrains the flexible tab 23 such that the proximal driver portion 7 is locked to the inner housing ensuring that the proximal driver 7 follows the path of the grooves in the inner housing. The axial movement of the locking member 11 also causes connector 19 to lock the distal driver portion 9 to proximal driver 7 to ensure that the distal portion of the driver moves in the same direction as the proximal driver. The connector 19 can be fixed to the distal driver as a separate component or can be an integral part of the distal driver formed during the molding or machining of the distal driver. The connector is in a connected position relative to the proximal driver during dose setting and dose delivery and is in an un-connected position in a preferred embodiment when the device is designed to be resettable, as explained below in more detail. Both the distal and proximal driver portions 9 and 7 are preferably generally cylindrical.

In an alternative embodiment, as shown in FIGS. 7-10, the flexible tabs are associated with locking member 11', preferably they are integral to the distal end of the locking member. Alternatively, the flexible tabs may be part of a separate component. FIG. 9 shows the locking member 11' in the un-locked proximal position during dose setting where the flexible tabs 21 are acting as a detent, riding in and out of the grooves of the inner body as the driver and locking member are rotated outwardly. FIG. 10 shows the locking member 11' in the locked position that occurs when the user pushes the injection button and urges the locking member forward (distally). This forward sliding motion causes the tabs to be locked into the grooves because the external surface of the driver acts as a blocking surface preventing the tabs from disengaging the grooves during dose delivery.

In normal use, the operation of the dose setting mechanism 4 occurs as follows. To dial a dose in the arrangement illustrated in FIGS. 4-6, a user rotates the dose dial grip 12. The proximal driver 7, the distal driver 9, the connector 10, the biasing element 13 and the number sleeve 3 rotate along with the dose dial grip 12. The number sleeve 3 extends in a proximal direction away from the housing 17. In this manner, the thread 15 of the distal driver 9 rotates over the spindle. At the limit of travel, a radial stop on the number sleeve 3 engages a stop provided on either the housing 17 or the inner housing 5 to prevent further movement. Rotation of the spindle is prevented because the thread 15 of the distal driver has the same lead as the external helical groove of the inner housing 5. A dose limiter 22, splined to the inner housing 5, may be included in a preferred embodiment and is advanced along the thread 23 of the distal driver by the rotation of the distal driver 9. As the driver rotates in the first direction (proximally) the flexible tabs override the grooves of the inner housing forming a detent.

When the desired dose has been dialed, the user may then dispense the desired dose by depressing the proximal face of the dial grip 12. As the user depresses the dial grip 12, this displaces a clutch (not shown), which ensures the dose dial sleeve and proximal driver move together during dose setting, axially with respect to the number sleeve 3, causing the clutch to disengage. Once the clutch is disengaged, the locking member will be urged forward to lock the flexible tabs into the grooves of the inner housing causing the proximal driver to follow the path of the groove. If the grooves are linear (straight), as shown in FIG. 2, the proximal driver will not rotate relative to the inner housing. If the grooves are helical, as shown in FIG. 3, the proximal driver will rotate relative to inner housing. The dose dial sleeve 3 and the dial grip 12 are free to rotate back to the starting position independent of the movement of the proximal driver. Because the proximal driver 7 is engaged with the distal driver 9 through the connector 19, the distal driver will move in the same direction along the same path as the proximal driver.

The driver is prevented from rotating with respect to the main housing 17 and inner housing 5 when the grooves in the inner housing are straight and parallel to axis of the inner housing, but the driver will rotate and move axially if the grooves are helical. In either case, the longitudinal axial movement of the drivers causes the spindle 10 to rotate and thereby to advance the piston or bung 20 in the cartridge to expel the dialed dose of medication through an attached needle assembly releasably connected to the distal end 8 of the cartridge holder 6.

In a preferred embodiment, after the drug delivery device has dispensed all of the medication contained in the cartridge, the user may wish to replace the empty cartridge in the cartridge holder 6 with a new cartridge. The user must then also reset the dose setting mechanism 4: for example, the user must then retract or push the spindle back into the dose setting mechanism 4. In order to retract the spindle of the arrangement shown in FIGS. 4-6, the distal portion and the proximal portion of the driver must be de-coupled from one another. The user may push the spindle, which in turn urges the distal portion of the driver in the proximal direction compressing biasing component 13 thus disengaging connector 19 from the proximal portion of the driver. After decoupling, the distal driver portion will be free to rotate relative to the proximal portion.

During a device resetting step, rotating the distal portion of the driver achieves at least two results. First, as the distal portion of the driver rotates it will reset the axial position of the spindle with respect to the dose setting mechanism 4 to a fully retracted position. Second, rotation of the distal portion of the driver will also axially move or reset dose limiter 22 to an initial or start position because the dose limiter is threadedly engaged to the outer threads 23 of the distal driver and is splined to the groove on the inner surface of the inner housing.

In this configuration, the dose limiter 22 is prevented from rotating but will move along the outer threads 23 of the distal driver portion 9 as this portion is rotated during a resetting step.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A drug delivery device having a driver locking feature comprising,
    a cartridge holder configured to contain a cartridge of medicament connected to a dose dialing assembly, where the dose dialing assembly comprises an outer housing and an inner stationary housing having at least one internal groove on an inner surface;
    a driver positioned within the inner housing; and
    a flexible tab integral with either the driver or a blocking member, where the tab engages the at least one internal groove to form a detent such that the tab disengages from the at least one internal groove during dose dialing,
    wherein the blocking member is positioned inside the driver, but is not threadedly engaged with the driver, and is configured such that the blocking member must slide relative to the driver to lock the flexible tab into the at least one internal groove to prevent disengagement of the tab from the at least one internal groove during dose dispensing such that the driver follows the path of the groove.

2. The drug delivery device of claim 1 where the flexible tab is an integral part of the driver.

3. The drug delivery device of claim 1 where the driver contains at least two flexible tabs.

4. The drug delivery device of claim 1 where the blocking member has an aperture that is aligned with the flexible tab when the blocking member is in a non-locked position and is misaligned with the flexible tab when in the locked position.

5. The drug delivery device of claim 4 where the flexible tab is locked in the at least one internal groove when the aperture is misaligned.

6. The drug delivery device of claim 1 where the at least one internal groove is parallel to a longitudinal axis of the inner housing.

7. The drug delivery device of claim 1 where the groove is helical along the axis of the inner housing.

8. A drug delivery device having a drive sleeve lockout feature comprising,
    a cartridge holder containing a cartridge of medicament connected to a dose dialing assembly, where the dose dialing assembly comprises an outer housing and an inner stationary housing having at least one internal groove on an inner surface;
    a driver positioned within the inner housing; and
    a locking member positioned inside the driver member and configured such that the locking member must slide relative to the driver and having a flexible tab that engages the at least one internal groove to form a detent such that the tab disengages from the at least one internal groove during dose dialing,
    wherein the locking member has a locked position during dose dispensing where the flexible tab is engaged with the driver to prevent disengagement of the flexible tab with the at least one internal groove such that the driver follows the path of the groove.

9. The drug delivery device of claim 8 where the driver has an aperture to receive the flexible tab.

10. The drug delivery device of claim 9 where the aperture is aligned with the flexible tab during dose dialing and is misaligned with the flexible tab during dose delivery.

11. A dose setting mechanism for a drug delivery device, said mechanism comprising:
- a proximal driver positioned inside a stationary inner housing having a inner surface;
- a clicker formed between the proximal driver and the inner surface of the inner housing, where the clicker forms a detent such that the clicker engages and disengages from at least one groove in the inner housing during dose setting and is locked to prevent disengagement of the clicker from the at least one internal groove in the inner housing during dose delivery; and
- a locking member that is must be axially slidable relative to the inner surface of the proximal driver, but is not threadedly engaged with the driver, and that engages the clicker during dose dispensing to lock the clicker into the at least on groove in the inner housing.

12. The dose setting mechanism of claim 11 further comprising a distal driver positioned inside the inner housing having a connector for engaging the proximal driver during dose setting and drug dispensing.

13. The dose setting mechanism of claim 12 further comprising a biasing member positioned between the proximal driver and the connector.

14. The dose setting mechanism of claim 11 where the clicker has at least one flexible arm that engages the at least one internal groove in the inner housing to form the detent during dose setting.

\* \* \* \* \*